US00PP25971P3

(12) United States Plant Patent
Olesen

(10) Patent No.: US PP25,971 P3
(45) Date of Patent: Oct. 6, 2015

(54) MINIATURE ROSE PLANT NAMED 'POULPAH064'

(50) Latin Name: ***Rosa* hybrid**
Varietal Denomination: Poulpah064

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 168 days.

(21) Appl. No.: 13/986,931

(22) Filed: Jun. 14, 2013

(65) Prior Publication Data

US 2014/0373207 P1 Dec. 18, 2014

(51) Int. Cl.
*A01H 5/02* (2006.01)

(52) U.S. Cl.
USPC ..... Plt./118

(58) Field of Classification Search
USPC ..... Plt./118
CPC ..... A01H 5/0222; A01H 5/0216; A01H 5/02; A01H 5/00
See application file for complete search history.

(56) References Cited

PUBLICATIONS

Help Me Find Poulpah064 Rose, retrieved on Jan. 12, 2015, retrieved from the Internet at <http://www.helpmefind.com/rose/pl.php?n=94975> one page.*

Upov Pluto Plant Variety Database 20141217, retrieved on Jan. 8, 2015, retrieved from the Internet at <www3.wipo.int/pluto/user/en/index.jsp> for *Rosa* Poulpah064 one page.*

* cited by examiner

*Primary Examiner* — June Hwu

(57) ABSTRACT

A new miniature rose plant that has abundant, yellow flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah064'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpah064', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant yellow flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah064' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah064' was selected by the inventor as a single plant from the progeny of the hybridization in 2007.

Asexual reproduction of 'Poulpah064' by vegetative stem cuttings was first done by Mogens N. Olesen in the nursery in Fredensborg, Denmark in 2008. This initial and other subsequent propagations conducted in controlled environments have demonstrated that the characteristics of 'Poulpah064' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah064'. Specifically illustrated in the drawing are flowers at various stages of development, flower in parts, leaves, and stems.

DETAILED DESCRIPTION OF THE VARIETY

The following is a description of 'Poulpah064', as observed in its growth in glasshouses in Half Moon Bay, Calif. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulsiv', U.S. Plant Pat. No. 13,104. are compared to 'Poulpah064' in Chart 1.

CHART 1

| | 'Poulpah064' | 'Poulsiv' |
|---|---|---|
| Petalage: | 35 petals, 3 to 5 of which are petaloids. | 50 to 55 petals under normal conditions with 3 to 5 petaloids |
| Flower Diameter: | 60 mm | 40 mm |
| General Tonality of Flower Color: | Yellow-Orange Group 14C with intonations of Yellow-Orange Group 22B | Yellow Group 8A to 8B |

FLOWER AND FLOWER BUD

Blooming habit: Continuous.

Flower bud:

*Size*.—Upon opening, 25 mm in length from base of receptacle to end of bud. 14 mm in diameter.

*Bud form*.—Urceolate.

*Bud color*.—As sepals unfold, petals are Yellow-Orange Group 15A.

*Sepals*.—Upper Surface: Color: Yellow-Green Group 147B. Texture: Smooth, moderately pubescent. Lower Surface: Color: Yellow-Green Group 146B. Texture: Smooth. Shape: Apex: Cirrhose. Base: Flat at union with receptacle. Margins: Margins have weak foliaceous appendages on three of the five sepals. Size: 30 mm long by 8 mm wide.

*Receptacle*.—Surface Texture: Smooth. Shape: Campanulate. Size: 8 mm tall and 7 mm wide. Color: Yellow Green Group 144B.

*Pedicel*.—Surface: Smooth. Length: 20 mm on average. Diameter: About 2.5 mm. Color: Yellow-Green Group 144B. Strength: Medium strength.

*Borne*.—Singly.

Flower bloom:

*Fragrance*.—Medium sweet floral scent.

*Duration*.—As a pot plant, flowers last up to 28 days.

*Size*.—Flower diameter is about 60 mm when open. Flower depth is 30 mm.

*Form*.—General shape is an open cup.

*Shape of flower, side view*.—Upon opening, the upper portion is convex. The lower portion is concave.

Petalage: Semi-double. About 35 petals, 3 to 5 of which are petaloids.

Color:

*General tonality*.—On open flower Yellow-Orange Group 14C with intonations of Yellow-Orange Group 22B. General tonality changes to.

*Upon opening, petals*.—Outermost petals are Yellow-Orange Group 16B with intonations of Yellow Group 13A towards the petal base on the upper surface. Yellow-Orange Group 19A on the lower surface with intonations of Yellow Group 13A towards the base. Innermost petals are Yellow Group 13A with intonations of Yellow-Orange Group 22A on the upper surface. Orange Group 24B with intonations of Yellow-Orange Group 15A at the margin on the lower surface.

*After opening, petals*.—Outermost petals are Yellow Group 13C, shaded with Yellow-Orange Group 22A on the upper surface. Yellow-Orange Group 15D on the lower surface with light intonations of Yellow-Orange Group 22B. Innermost petals are Yellow-Orange Group 14C on the upper surface. Yellow-Orange Group 16B on the lower surface.

Petals:

*Petal reflex*.—Weak.

*Margin*.—Entire, with strong undulations.

*Shape*.—Generally rounded. Apex shape: Rounded. Base shape: Rounded.

*Size*.—32 mm (l) by 34 mm (w).

*Texture*.—Smooth.

*Thickness*.—Average.

Petaloids:

*Quantity*.—About 3 to 5.

*Shape*.—Apex and base are Rounded.

*Color*.—Yellow-Orange Group 14A on the upper surface. Yellow-Orange Group 16A on the lower surface.

*Size*.—15 mm (l) by 15 mm (w).

Reproductive organs:

*Pollen*.—None Observed.

*Anthers*.—Size: 2 mm long. Color: Yellow Group 13A. Quantity: 30 on average.

*Filaments*.—Color: Yellow-Orange Group 17A. Length: About 5 mm.

*Pistils*.—Length: About 4 mm long. Quantity: 15 on average.

*Stigmas*.—Slightly inferior relative to the length of the filaments and the height of the anthers. Color: Yellow-Green Group 150D.

*Styles*.—Color: Yellow-Green Group 150D.

*Seed formation*.—Not observed.

PLANT

Plant growth: Upright. Plants are 20 cm in height, and 15 cm wide.

Stems:

*Color*.—Juvenile growth: Yellow-Green Group 144B. Mature growth: Yellow-Green Group 144A.

*Length*.—Canes are 12 cm from the base of the plant to the flowering portion.

*Diameter*.—3 mm.

*Internodes*.—On mature canes, there is an average distance of 15 mm between nodes.

*Surface texture*.—Young and mature wood is smooth.

Prickles: Few small pickles 1 mm in length, Yellow Green 145C. Long prickles not observed.

Plant foliage:

*Compound leaf size*.—80 mm (l) by 65 mm (w).

*Leaf bearing angle to the stem*.—60 to 90 degrees.

*Quantity*.—4 to 5 leaves per 10 cm of stem.

*Color of juvenile foliage*.—Upper Leaf Surface: Yellow-Green Group 146C. Lower Leaf Surface: Yellow-Green Group 146C. Anthocyanin: Greyed-Purple Group 183A at the margins of the upper surface and shaded underneath.

*Color of mature foliage*.—Upper Leaf Surface: Yellow-Green Group 147A. Lower Leaf Surface: Yellow-Green Group 147B.

Plant leaves and leaflets:

*Stipules*.—Size: About 9 mm in length. Shape: Linear, slightly broad based with outward extending apecies.

Margins: Finely serrated with few stipitate glands. Color: Yellow-Green Group 144A.

*Petiole*.—Length: 15 mm on average. Diameter: About 1 mm. Upper surface: Yellow-Green Group 144A. Lower surface: Yellow-Green Group 144B.

*Rachis*.—Length: 25 mm on average. Diameter: About 1 mm. Upper surface: Yellow-Green Group 144A with intonations of Greyed-Purple Group 183A. Lower surface: Yellow-Green Group 144B.

*Leaflet*.—Number of leaflets: 5 on normal leaves in middle of the stem. Size: On average 50 mm in length by 32 mm wide. Margin: Serrate. General Shape: Ovate. Apex Shape: Cuspidate. Base Shape: Round. Texture: Smooth. Arrangement: Odd pinnate. Venation: Reticulate. Leaf Gloss: Not glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: Average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

The invention claimed is:

1. A new and distinct variety of rose plant of the miniature class named 'Poulpah064', substantially as illustrated and described herein, due to its abundant, yellow flowers, vigorous growth, compact habit, suitability for production from softwood cuttings in pots, and durable flowers and foliage that make the variety suitable for distribution in the floral industry.

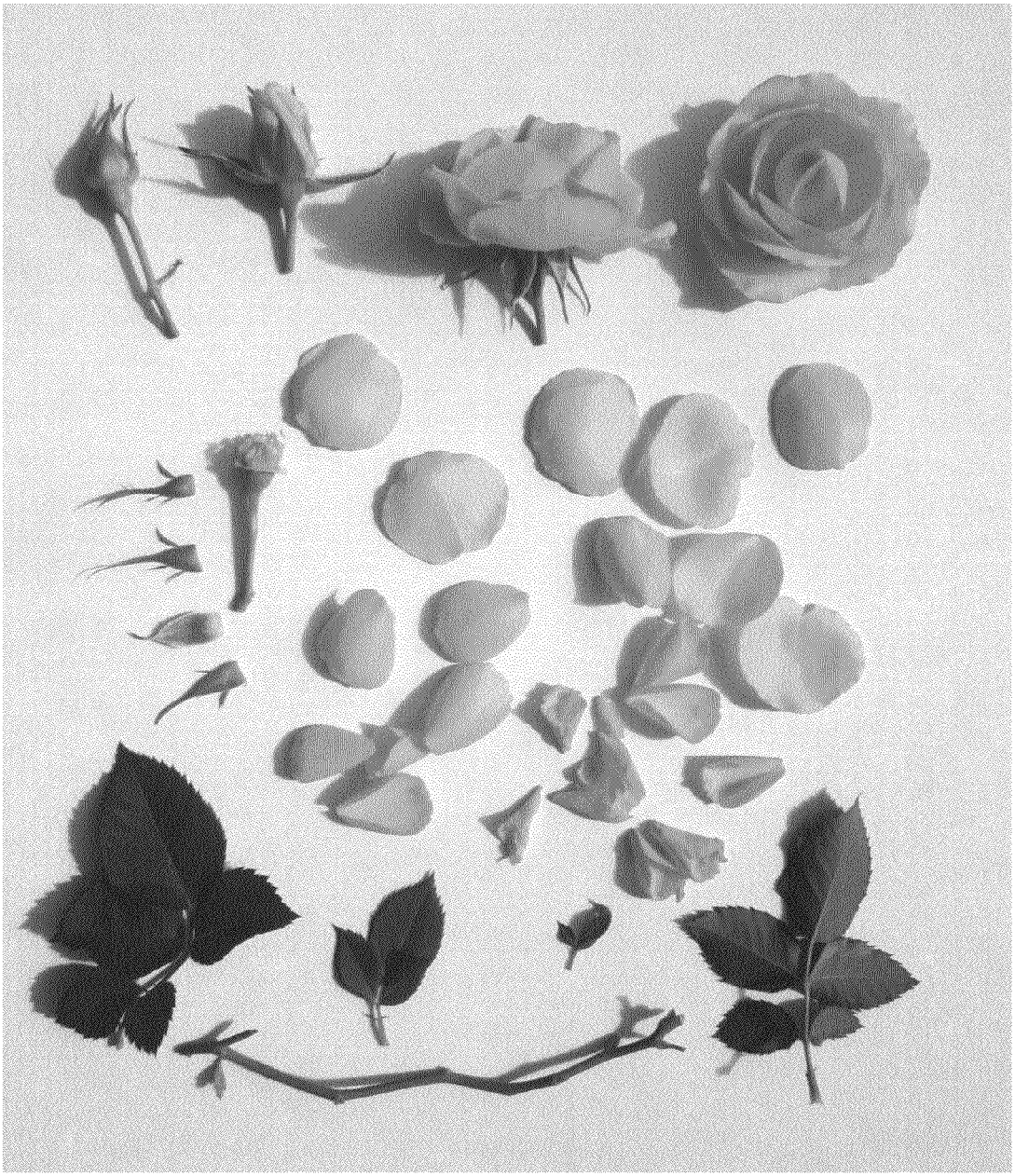

* * * * *